United States Patent
Wolter

(10) Patent No.: US 7,432,385 B2
(45) Date of Patent: Oct. 7, 2008

(54) PHOSPHOROUS-CONTAINING, ORGANIC POLYMERISABLE SILANES AND SILICIC ACID POLYCONDENSATES PRODUCED THEREWITH

(75) Inventor: Herbert Wolter, Tauberbischofsheim (DE)

(73) Assignee: Fraunhofer-Gesellschaft zur Foerderung der Angewandten Forschung E.V., Muechen (DE)

( * ) Notice: Subject to any disclaimer, the term of this patent is extended or adjusted under 35 U.S.C. 154(b) by 573 days.

(21) Appl. No.: 10/471,414

(22) PCT Filed: Mar. 12, 2002

(86) PCT No.: PCT/EP02/02715

§ 371 (c)(1),
(2), (4) Date: Mar. 8, 2004

(87) PCT Pub. No.: WO02/088222

PCT Pub. Date: Jul. 11, 2002

(65) Prior Publication Data

US 2004/0138490 A1  Jul. 15, 2004

(51) Int. Cl.
*C07F 9/02* (2006.01)
(52) U.S. Cl. ..................................... 556/405
(58) Field of Classification Search ............... None
See application file for complete search history.

(56) References Cited

U.S. PATENT DOCUMENTS

| 4,772,408 A | 9/1988 | Mohr et al. |
| 6,111,002 A | 8/2000 | Doring et al. |
| 6,172,131 B1 | 1/2001 | Moszner et al. |

FOREIGN PATENT DOCUMENTS

| DE | 22 19 983 | 11/1973 |
| DE | 27 58 414 A | 7/1979 |
| DE | 40 11 044 A | 10/1991 |
| DE | 41 33 494 C2 | 4/1993 |
| DE | 43 10 733 A | 10/1994 |
| DE | 44 16 857 C | 6/1995 |
| DE | 44 05 261 A1 | 8/1995 |
| DE | 197 46 708 A1 | 4/1999 |
| DE | 198 32 094 A1 | 1/2000 |
| EP | 0 525 573 A1 | 2/1993 |

OTHER PUBLICATIONS

Chemical Abstract 1968:49754; Abstract of SU 199874; 7/1967.*
Moszner, N., et al., "Synthesis and radical polymerization of hydrolytically stable acrylic phosphonic acids", Macromol. Chem. Phys. 200, pp. 1062-1067 (1999).
Patent Abstracts of Japan, No. 11246572 A, (Ivoclar, AG), Sep. 14, 1999.

* cited by examiner

Primary Examiner—Samuel A Barts
(74) Attorney, Agent, or Firm—Stephen A. Bent; Steven M. Reid; Foley & Lardner LLP

(57) ABSTRACT

The invention relates to compounds of formula (I) $(X_aR_bSi)_m[(B)([O]_oP[O]_pR'_cY_d)_n]_{4-a-b}$ (I), where the groups, residues and indices have the following meanings: B=an at least doubly-valent straight chained or branched group with at least one organic polymerizable group and at least three carbon atoms, X=a group which may be cleaved from the silicon atom by hydrolysis, R=optionally substituted alkyl, alkanyl, aryl, alkylaryl or arylalkyl, R'=R, Y=Cl, OH or OR', R"=H, alkyl or aryl, a=0, 1, 2 or 3, b=0, 1 or 2, a+b together=1, 2 or 3, c=0, 1 or 2, d=0, 1 or 2, c+d together=2, m=at least 1, with the proviso that m is not greater than 1 when a+b=1 or 2, n=at least 1, o=0 or 1 and p=0 or 1. The invention further relates to a series of methods by which the above compounds may be produced.

13 Claims, No Drawings

PHOSPHOROUS-CONTAINING, ORGANIC POLYMERISABLE SILANES AND SILICIC ACID POLYCONDENSATES PRODUCED THEREWITH

The present invention relates to novel molecules, which comprise at least one silane group with possibly hydrolysable radicals, at least one organically polymerisable group and at least one reactive phosphorous-containing group or phosphorous-containing group that modulates the properties of the molecule, respectively. Moreover the invention relates to hydrolysis and condensation products of these molecules, which were produced while using said molecules. And finally the invention relates to a method for producing the inventive molecules.

Silicic acid hetero-polycondensates, which can be obtained through the hydrolysis and condensation of silanes with hydrolysable groups, have been known for a long time (see e.g. DE PS 27 58 414). Such condensates can be processed into various products, for example into protective layers, coatings, membranes or bulk materials. The underlying silanes can also comprise double bonds or other organically reactive groups, through which they can be polymerized into an organic network (see e.g. DE 40 1.1 044 C2 and DE 44 05 261 A1). Such materials can be used for example in the production of dental materials (see e.g. 41 33 494 C2).

We also know of silane compounds, which have a phosphorous-containing group in the molecule. It has long been known about phosphorous-containing materials that they can have flame-retarding properties. DE 198 32 094 A1 suggests to mix dispersions comprising at least one water insoluble organo-polymer and a water-dispersible silicon compound with a dispersible phosphorous compound in order to make the textile materials produced from the dispersions flame-resistant. In a special design the phosphorous compounds used are such compounds, which additionally carry one silicon atom in the molecule, for example triethoxy silyl ethane phosphoric acid diethyl ester, which is commercially available. Pursuant to EP 525 573 A1 it is supposed to be possible to use phosphorous-group containing organo-silanes as immuno-regulators. U.S. Pat. No. 4,772,408 suggests phosphonate silanes as stabilizers for anti-freezes.

The synthesis of above-mentioned phosphorous-containing silanes can in principle occur via two methods: Either a silane containing an organic double bond is reacted with a P—H bond of a phosphonate or the like, or an alkoxy group on the phosphorous is reacted with a halogen.

It is the object of the present invention to provide novel inorganic-organic resins that are obtained through the hydrolysis and condensation of silane-containing educts, wherein monomers comprising phosphorous-containing groups can be or have been condensed into said resins. The presence of the phosphorous-containing groups shall convey modified properties to these materials and/or the coatings or bulk materials produced thereof either through their chemical functionality (e.g. reaction with complexable groups) or their physical properties (e.g. improved flame resistance, higher polarity). Additionally it is the object of the invention to provide a novel group of compounds, which are suited for the production of such resins and which beyond that enable improved bonding with inorganic and/or organic constituents of said resins.

Pursuant to the invention compounds are made available that contain a hydrolysable silane radical or its hydrolysis products, a reactive phosphorous-containing radical or a phosphorous-containing radical, which upon incorporation of the compounds in an inorganic and/or organic network modulates the network's properties, as well as an organically polymerisable radical.

All three molecules can be used for property modification purposes in accordance with JTB (ISC) 1992, p. 61-72 and Polymer+Materials Research Symposium 1993, Bayreuth, Germany, p. 14-17. The phosphorous-containing molecule part hereby offers the masses produced with the inventive compounds additional variability, which leads to special and novel combinations of characteristics.

With the help of such compounds either the aforementioned resins can be produced, which in turn can be used to produce organic cross-linked products, or they can be processed directly into organic polymerizates, which may subsequently be further cross-linked through the hydrolysis and possible condensation of the developing groups.

Accordingly the invention provides compounds of the formula I

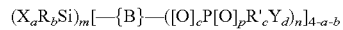   I wherein the radicals and indices have the following meaning:

B is a straight-chained or branched radical with at least one organic polymerisable group, which is preferably a C=C double bond, and at least 3, rather 4, and preferably up to 50 carbon atoms, X is a radical that can be cleaved from the silicon atom by hydrolysis, especially hydrogen, halogen and here preferably chlorine, hydroxy, alkoxy with preferably 1 to 4 carbon atoms, acyloxy with preferably 2 to 5 carbon atoms, alkylcarbonyl with preferably 2 to 6 carbon atoms, alkoxycarbonyl with preferably 2 to 6 carbon atoms or NR" and can possibly have different meanings in a compound of the formula I, R is possibly substituted alkyl, alkenyl, aryl, alkylaryl or arylalkyl with preferably 1-6 carbon atoms for open-chained aliphatic groups and preferably 6 to 12 carbon atoms for cyclo-aliphatic or aromatic groups, wherein the substitution can occur for example with halogen or amino groups, oxygen-containing and/or sulfur-containing radicals, R' can have the same meaning as R, Y is Cl, OH or OR', R" is hydrogen, alkyl with preferably 1-4 carbon atoms or aryl with preferably 6-12 carbon atoms, a is 0, 1, 2 or 3, b is 0, 1 or 2, a+b together are 1, 2 or 3, c is 0, 1 or 2, d is 0, 1 or 2, c+d together are 2, m is preferably 1, but can also be 2, 3, 4 or possibly even a higher number, but only when a+b means 3, n is preferably 1, but can also be 2, 3, 4 or possibly even a higher number, o is 0 or 1, and p is 0 or 1.

B is a radical with at least 2 bonds (namely at least one to the phosphorous-containing group and at least one to the silane group). When m and/or n are greater than 1, several silane- or phosphorous-containing radicals are bound to respectively different atoms (e.g. C atoms) in the radical B, the number of these bonds of B then increases accordingly. When a+b together are 1 or 2, the number of B-containing radicals on the silicon, which is defined at 4-a-b, becomes 2 or 3.

This means that the silicon atom is arranged between two or even 3 such groups. In such cases, however, according to the definition m should be equal to 1 (otherwise Formula I would also comprise poly-condensates). Designs with a+b equal 1 or 2 are possible above all when the radical B is not very complex from a steric point of view.

B itself can contain the or at least one of the organic polymerisable groups in its main chain (i.e. in the chain that bonds the phosphorous-containing radical and the silane radical); frequently this group or at least one of these groups can be found in a side chain. The organic polymerisable group(s) can be selected randomly. They can be e.g. vinyl, allyl, norbornen, glycidyl, acryl or methacryl groups. Preferably B is derived from a substituted or unsubstituted compound with acrylate or methacrylate groups. B can comprise a continuous carbon skeleton, the carbon chain(s) (main and/or side chain(s)) however can also be interrupted by hetero-atoms or groups such as O, S, SO, NH, NHCO, PR, POR, CONHCO, COO, NHCOO or the like. Moreover, B can be bound to the silane radical via such groups. The carbon skeleton can be exclusively aliphatic, with open and/or closed structures. B however can also comprise one or more aromatic core(s) or condensed systems or triazine groups or the like, e.g. bisphenol-A structures or the like. Furthermore the groups or structure can be randomly substituted, e.g. with acid, acid amide, ester or amino groups.

In a preferred design, B comprises at least one acrylate or methacrylate group. As will be explained in the following in the description of possible manufacturing methods for the inventive compounds, it is particularly preferred—proceeding from oligo- or poly-acrylates or methacrylates with at least three 3 (meth)acryl groups—to arrive at compounds in which B represents a radical in which at least 2 (meth)acrylate groups were reacted with at least one phosphorous-containing molecule and at least one silane molecule or its precursor so that the radical B comprises at least 2 fewer (meth)acrylate groups than the oligo- or poly(meth)acrylate, which was used to produce the inventive compound. Instead however it is also possible to proceed from oligo- or polyacrylates or methacrylates, which compared to the compounds of the present invention comprise one additional (meth)acrylate group if these (meth)acrylates additionally contain a hydroxy group, via which e.g. an isocyanatosilane can be coupled. Instead of (meth)acrylates of course other organic polymerisable radicals, e.g. alkylene oxide groups, especially glycide ether groups, or vinyl or allyl or norbomen groups are suited as well. Several different such groups in B or its precursor are also possible in principle. Particular preferred as structural elements of B are among other things the trimethylolpropane group, the penta-erythritol group and the glycerol structure.

The groups containing the phosphorous can be selected from phosphates (esters of phosphoric acid $H_3PO_2$), phosphonates (esters of phosphonic acid $HP(O)(OH)_2$), trialkyl esters of the phosphorous acid tautomeric with the phosphonic acid, esters of the phosphinic acid $H_2P(O)(OH)$, trialkyl/arylphosphine oxides and trialkyl/arylphosphines, wherein generally the "acid protons" of the underlying acid, with said protons being located on the phosphorous, are replaced by an alkyl group and the hydroxy groups of the underlying acid by alkoxy groups. The radical $(X_BR_bSi)_m$—{B}-hereby preferably exists directly bonded to the phosphorous atom (i.e. o is zero) since the phosphoric acid ester groups tend to cleave in an aqueous medium by hydrolysis so that such molecules are less stable at least in a certain environment. Due to their properties, which will be explained further below, esters of the phosphonic acid and esters of the phosphinic acid are preferred the most.

Accordingly in the group $[O]_oP[O]_pR'_cY_d$ of Formula I in preferred designs of the invention o is equal to zero. Similarly preferred is c equal to 0 or 1, and particularly preferred is c equal 0. In all these designs that are mentioned as being preferred, p is preferably 1. R' is preferably alkyl or aryl, especially methyl, ethyl, n- or iso-propyl or n-, iso- or t-butyl, and Y is preferably alkoxy or aryloxy, especially methoxy, ethoxy, n- or iso-propoxy or n-, iso- or b-butoxy. Instead the phosphonic acid or phosphinic acid esters can also exist in hydrolysed form, i.e. Y can also mean hydroxy.

The substituents or radical X and R located on the silicon atom can be selected randomly. In literature about materials containing inorganic-organic silicon atoms, e.g. such that are commercially available under the term "ORMOCER"®, much has been written about the respective properties, which the respective silane radicals convey to the condensate or organic polymerized network, so that no detailed explanations are required in this respect. X signifies hydrolysable radicals. With these groups, which are also called inorganic network formers, in cooperation with possibly existing organic network formers, namely organic polymerisable groups (in the present case also the group(s) [—{B}—$([O]_oP[O]_pR'_cY_d)_n$], physical properties of the developing network are adjusted, such as hardness or flexibility, thermal stability, thermal coefficient of expansion. The not organic polymerisable groups R are described as network modifiers; through their selection also a series of properties can be influenced.

The production of the inventive compounds can occur in many different ways.

A first method starts with compounds II

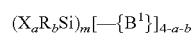  II wherein X, R, a, b and m have the meanings as defined in Formula I and $B^1$ is a group, which comprises one C=C double bond more than group B. These compounds are reacted with

  III, wherein R', Y, c and d can have the aforementioned meanings and p is 1. The hydride reacts with one of the double bonds on the group $B^1$ while forming the group —$CHR^1$—$CR^2R^3$—$P[O]_pR'_cY_d$, wherein the group —$CHR^1$—$CR^2R^3$ is a part of B. This way phosphonic acid ester derivatives and phosphinic acid ester derivates can be produced. The reaction occurs preferably while adding a radical (e.g. for non-activated double bonds) or alkaline (e.g. for activated double bonds) catalyst, e.g. a sodium alcoholate. It is particularly advantageous if the double bond of $B^1$ that is involved in the reaction is part of a Michael system, e.g. part of a (meth)acrylate group. In the compound III, d can mean for example 2 and Y can be an alkoxy group, or c and d can each mean 1 and R' can be an alkyl group and Y an alkoxy group.

A second method proceeds from compounds IV

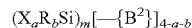  IV, wherein X, R, a, b and m have the meanings as defined in Formula I and $B^2$ is a group, which comprises one OH group more than group B. These compounds are reacted in the presence of an alkaline catalyst with $POCl_3$, wherein a group $(X_aR_bSi)_m$—{B}—$]_{4-a-b}$O is bound to the phosphorous atom with simultaneous cleavage of HCl. The remaining chloride atoms are subsequently displaced, possibly through reaction with suitable alcoholates; both the chloride and alcoholate groups are open to hydrolysis later on. During this reaction, which leads to phosphoric acid esters, a slightly careless conduction of the reaction with mixtures of the desired reaction product can easily lead to products in which the silane has been added twice so that cleaning steps may be required.

A third method utilizes the reaction of compound IV with phosphorous pentoxide. The product is a corresponding phosphoric acid mono-ester of the formula I, wherein Y is OH, o and p are 1, c is zero and d is 2.

A fourth method employs the Arbuzov Reaction. Hereby compounds V

     V, wherein $B^3$ is a group deduced from B, which contains an additional halogen atom, are reacted with phosphorous compounds of the formula VI,

     VI wherein R' and Y have the meanings provided for Formula I and c is 0, 1 or 2, d is 1, 2 or 3 and c+d is 3. If phosphorous compounds VI are used, in which c is equal 0, phosphonic acid esters are obtained. If phosphorous compounds VI are used, in which c is equal 1, phosphinic acid esters are produced, and if phosphorous compounds VI are used, in which c is equal 2, phosphine oxide compounds are obtained.

The above-mentioned reaction methods for the production of compounds I are of course not exhaustive. For example compounds can be produced in other ways, wherein additional functional groups are introduced into the radical B. One example is the reaction of compounds of the formula III with silanes of the formula IV, which however instead of a hydroxy group comprise additionally an aldehyde group, and subsequently with an acid chloride in the presence of a silane:

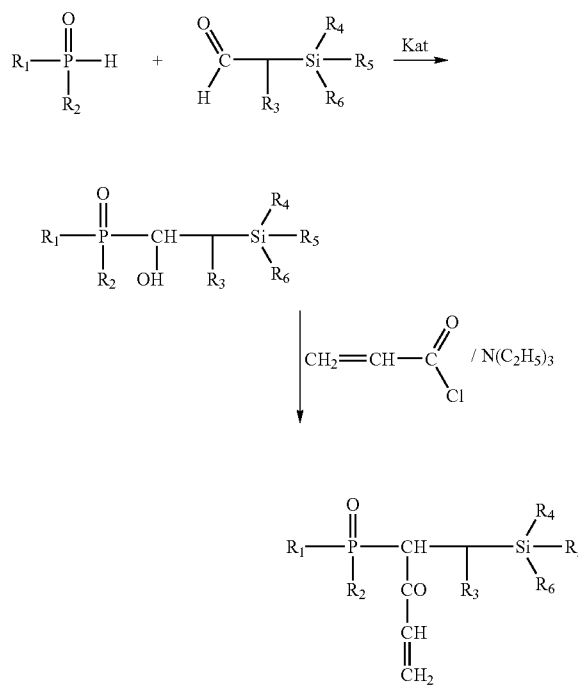

Such reactions are also possible e.g. with appropriate ketones instead of the aldehydes.

Silanes of the formulas II and IV are known in great numbers. Compounds of the formula II can be produced for example in that a silane of the general Formula VII

     VII in which X and R are defined as in Formula I, a+b is 3, $R^4$ is alkyl, arylene or alkylene-arylene and D means the group SH, $PR^5H$ or $POR^5H$ with $R^5$ being hydrogen, alkyl or aryl, is subjected to an addition reaction with a compound $B^4$, which comprises one C=C double bond more than the Group $B^1$ in Formula II. In the developing product with the Formula II, $B^1$ is bound to the silicon atom via a group $R^4D'$ with D' equal S, $PR^5$ or $POR^6$.

Alternatively, silanes of the Formulas II and IV can be produced in that a silane of the formula

     VIII wherein X, R, a, b and $R^4$ have the same meanings as in Formula VII, is subjected to condensation reaction with a compound $B^5$, which is a hydroxy- or amino- or SH-substituted derivative of the Group $B^1$ in Formula II. In the developing product with the Formula II, $B^1$ is bound to the silicon atom via a group $R^4D'$ with D' equal NHC(O)O.

Moreover silanes of the Formulas II and IV can be produced e.g. in that a silane with the Formula IX

     IX wherein X, R, a and B have the same meanings as in Formula VII, is subjected to hydrosilylation reaction with a compound $B^4$, which comprises one C=C double bond more than the Group $B^1$ in Formula II.

Compounds of the Formula IV can be obtained in the same manner, wherein instead of the compounds $B^4$ or $B^5$ compounds $B^6$ are used, which compared to the compounds $B^4$ and $B^5$ contain one hydroxy group (more).

Examples for such compounds can be found e.g. in DE 41 33 494 A1, DE 43 10 733 A1, DE 44 05 261, DE 44 16 857 A1 or DE 198 32 965 A1.

For the expert it is evident that the aforementioned production processes, in all of which the phosphorous-containing group is coupled last to the molecule that is to be produced, can also be reversed, i.e. that first the phosphorous-containing group is bound to the corresponding derivatives of B and then the silicon-containing group.

If the compounds of Formula I contain groups X and/or Y in the molecule, they can be subjected to hydrolysis. Since the hydrolysis conditions can deviate for groups Y from those for groups X, especially when X and Y are alkoxy groups, hydrolysis can occur selectively. Alkoxy groups are for example cleaved from the silicon atom in the presence of water and possibly a solvent already under mild conditions; they remain on the phosphorous atom. The hydrolysis of alkoxy groups on the phosphorous atom by contrast succeeds specifically in the presence of trimethyl silyl bromide and methanol as the catalyst. Under more acidic conditions (for example in an aqueous-acidic medium at elevated temperatures), the groups can be cleaved from both types of atoms.

The following shall clarify this:
1. Hydrolysis of the phosphonate and alkoxy group
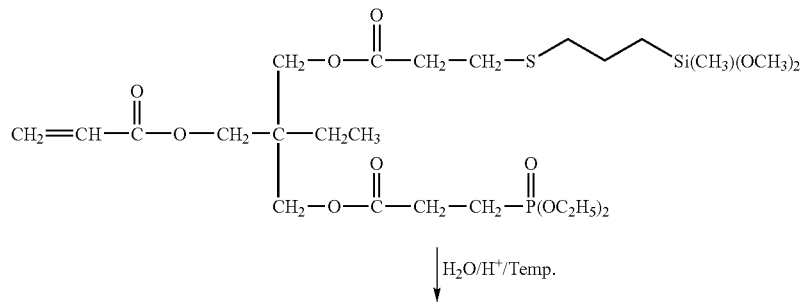
2. Selective hydrolysis of the alkoxy group possible
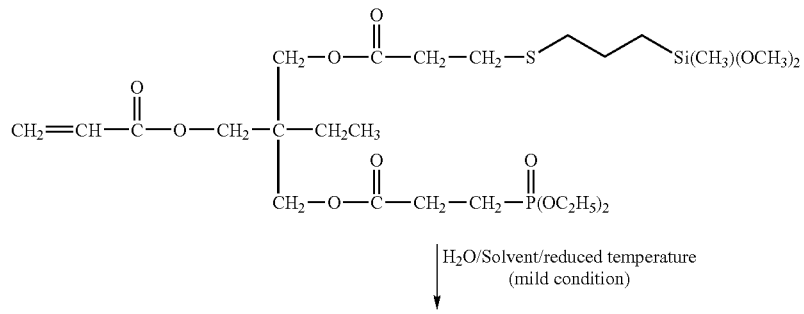
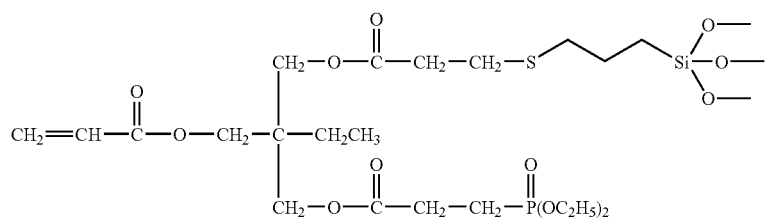

3. Selective hydrolysis of the phosphonate possible

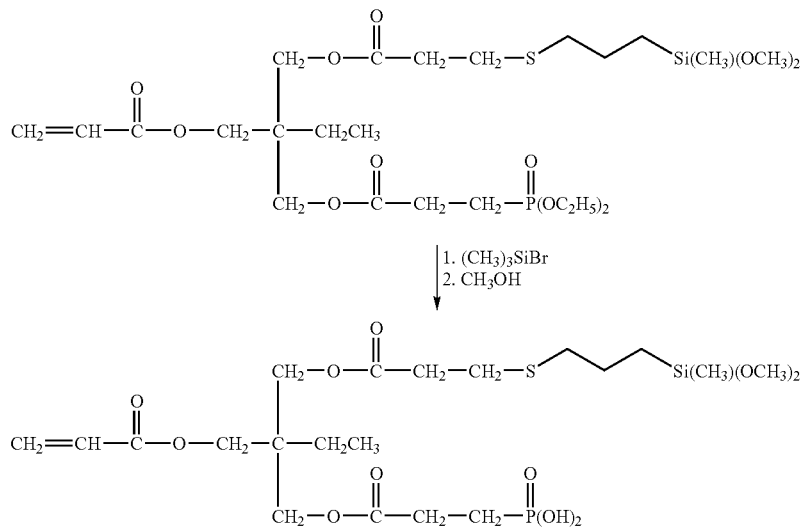

The inventive compounds of the Formula I can be embedded in inorganic networks with Si—O—Si units if they contain hydrolysable or hydrolysed radicals on the silicon atom. Moreover they are supposed to be able to be embedded in organic polymer structures by means of the radicals B, or such structures are supposed to be able to be built by means of the organic polymerisable groups of the radicals B. Inorganic condensed silicic acid hetero-polycondensates and products that can be obtained through the organic cross-linkage of such condensates are known in larger numbers. In principle they are produced based on a sol-gel process. The condensates can be used in various applications, e.g. as molding compounds, as paints for coatings and the like.

If the inventive compounds of the Formula I contain groups X, they can be hydrolysed and condensed in an alkaline or acidic environment without already causing a cross-linkage via the organic polymerisable groups into the developing polymerisate. This way it is possible to embed them in any random networks, which can consist either exclusively of compounds of the Formula I or also of a mixture with other silanes, as we know them from the prior art. Moreover it should be possible to build an organic network through polymerization of the organic groups contained in the radical B. This allows these compounds to be used in a variety of coating, filling, adhesion and sealing compounds as molded bodies and embedding compounds.

The present invention accordingly furthermore provides silicic acid polycondensates, which are produced while including silanes of the general Formula X

    X.

In the silanes of the Formula X the radicals and indices have the following meaning:

$B^7$ is a straight-chained or branched radical with possibly one or more organic polymerisable group, preferably a C=C double bond, and at least 1, preferably 2 to 50 carbon atoms, X is a radical that can be cleaved from the silicon atom by hydrolysis, especially hydrogen, halogen and here preferably chlorine, hydroxy, alkoxy with preferably 1 to 4 carbon atoms, acyloxy with preferably 2 to 5 carbon atoms, alkylcarbonyl with preferably 2 to 6 carbon atoms, alkoxycarbonyl with preferably 2 to 6 carbon atoms or NR" and can possibly have different meanings in a compound of the formula I, R is possibly substituted alkyl, alkenyl, aryl, alkylaryl or arylalkyl with preferably 1-6 carbon atoms for open-chained aliphatic groups and preferably 6 to 12 carbon atoms for cyclo-aliphatic or aromatic groups, wherein the substitution can occur for example with halogen or amino groups, R' can have the same meaning as R, Y is Cl, OH or OR', R" is hydrogen, alkyl with preferably 1-4 carbon atoms or aryl with preferably 6-12 carbon atoms, a is 0, 1, 2 or 3, b is 0, 1 or 2, a+b together are 1, 2 or 3, c is 0, 1 or 2, d is 0, 1 or 2, c+d together are 2, m is preferably 1, but can also be 2, 3, 4 or possibly an even higher number, but only when m is no greater than 1, when a+b means 1 or 2, n is preferably 1, but can also be 2, 3, 4 or possibly an even higher number, o is 0 or 1, and p is 0 or 1.

The polycondensates can be composed exclusively of compounds of the Formula X; however they can also form the aforementioned polycondensate together with further hydrolysed silanes and/or other metal compounds and/or filling agents and/or adjuvants. The polycondensates are obtained through hydrolysis and condensation of the silane compounds of the Formula X, if necessary in the presence of further substances that are to be embedded, e.g. condensation catalysts, as we know them from the state of the art.

The inventive silicic acid polycondensates can be used in a variety of applications. Here we would only like to mention coating masses, binding agents for ceramic particles, adhesives or casting compounds by way of example. The presence of phosphorous-containing radicals in the polycondensates or coatings or compounds as mentioned above offers the products properties not known until now. Apart from the aforementioned improvement of flame resistance, the following should be mentioned: Since the phosphorous-containing radical is a charge carrier, the behavior of the polycondensates in dispersions or emulsions is modified. This can be beneficial when they are used in electrophoretic enamelling processes. The compounds produced this way exhibit a modified conducting behavior and different anti-static behavior. Products should exhibit improved corrosion protection behavior. The solubility of compounds of the Formula I in polar solvents is better so that it is possible to process them in another spectrum of solvents.

The following shall explain the invention in more detail based on examples.

EXAMPLE 1

Reaction of trimethylolpropane triacrylate with 3-mercaptopropylmethyldimethyloxy silane (described in DE-PS 40 11 044 and EP 0451709) and subsequently with diethyl phosphite.

Reaction Process:

Reaction of a dimethyl acrylate silane with diethyl phosphite and subsequent hydrolysis and condensation

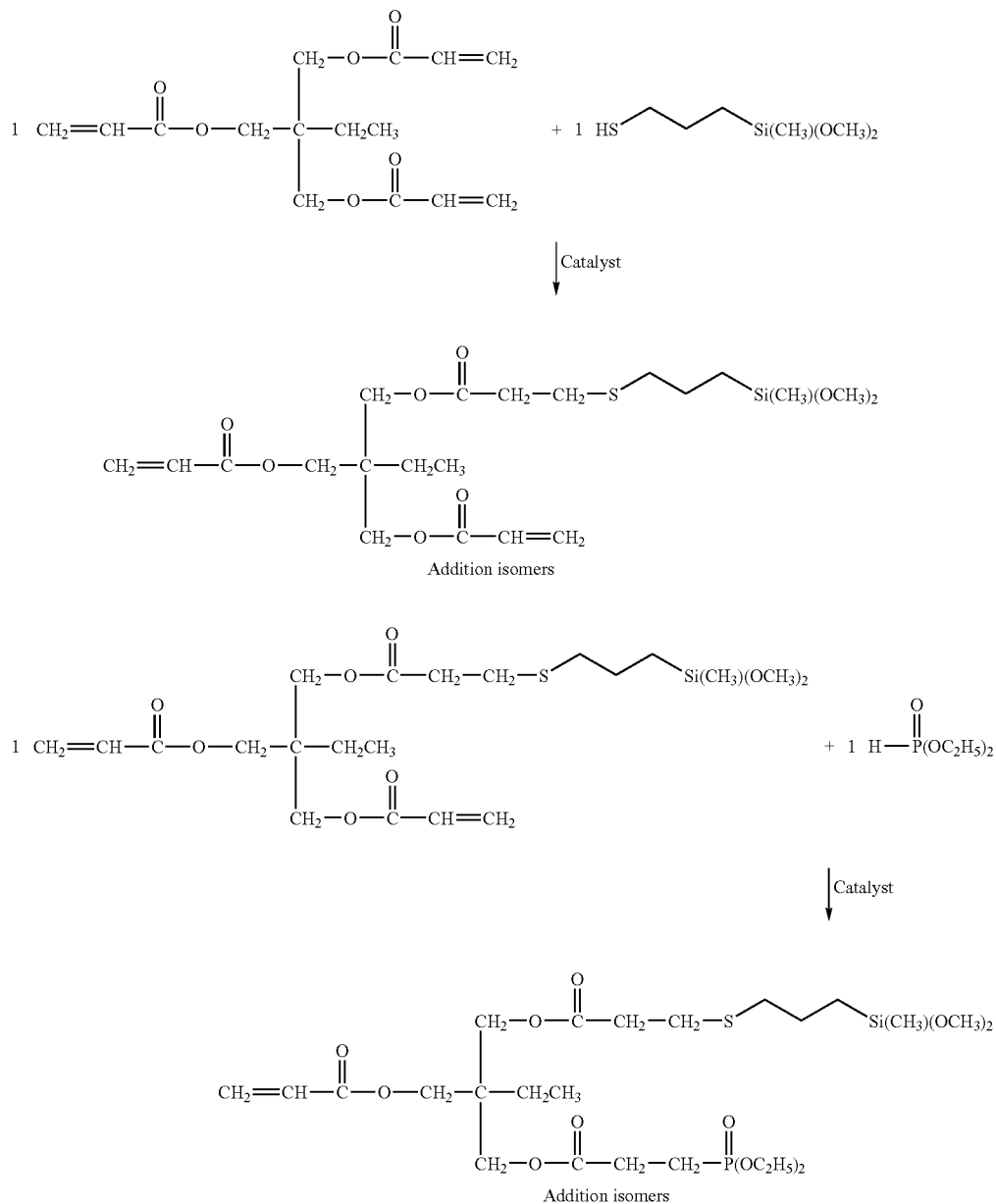

-continued

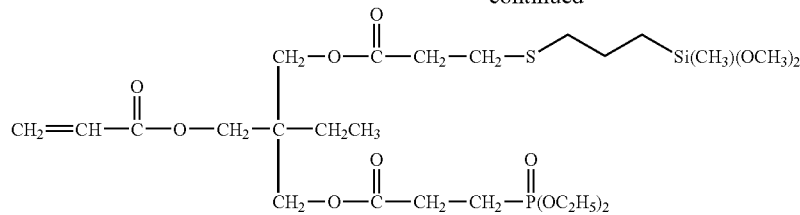

↓ Hydrolysis/Condensation/Working Up

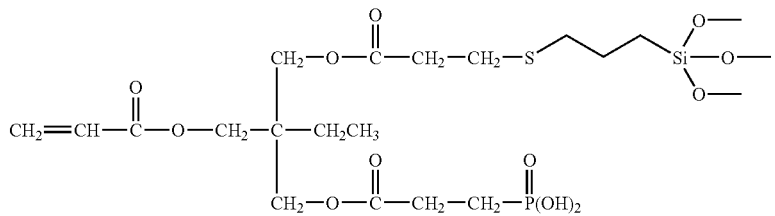

Under cooling conditions, a dry protective gas atmosphere and stirring, 1.06 g of an ethanolic KOH solution is added dropwise to 4.61 g (15.5 mmol) trimethylolpropane triacrylate (TMPTA). Under the same conditions, 2.80 g (15.5 mmol) 3-mercaptopropylmethyldimethoxy silane are added dropwise, wherein the temperature in the reaction vessel rises slightly. In about 5 minutes, the SH groups are completed converted (can be proven with the iodine test), and the reaction (thiol addition) has been completed. The resulting clear reaction mixture is first mixed with 2.13 g diethyl phosphite (15.5 mmol) under the aforementioned conditions and subsequently with a 25% sodium methanolate solution as the catalyst. The course of the reaction and thus the complete conversion of this exothermic PH addition can be proven by means of IR spectroscopy based on the following changes:

disappearance of the $v_{PH}$ bands at 2431 cm$^{-1}$
decrease of the $v_{CH}$ bands (olefin) at 3040 cm$^{-1}$
decrease of the $v_{C=C}$ bands at 1635/1619 cm$^1$ The resulting phosphonate-modified acrylate silane (isomer mixture) can also be isolated in the form of a viscous liquid through usual processing or preferably directly reacted further.

EXAMPLE 2

Reaction of glycerine-1,3-dimethacrylate with 3-isocyanate propyl triethoxy silane (described in DE-PS 40 11 044 and EP 0451709) and subsequently with diethyl phosphite Reaction Process:

Reaction of a diacrylate silane with diethyl phosphite and subsequent hydrolysis and condensation

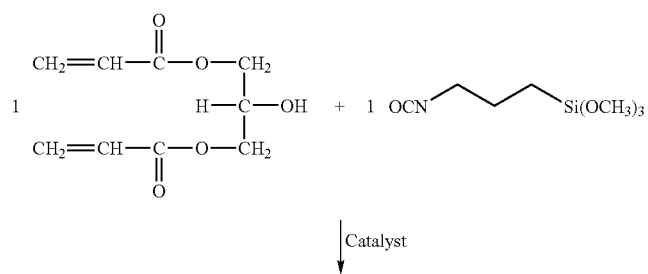

↓ Catalyst

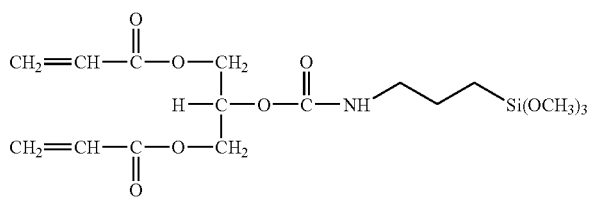

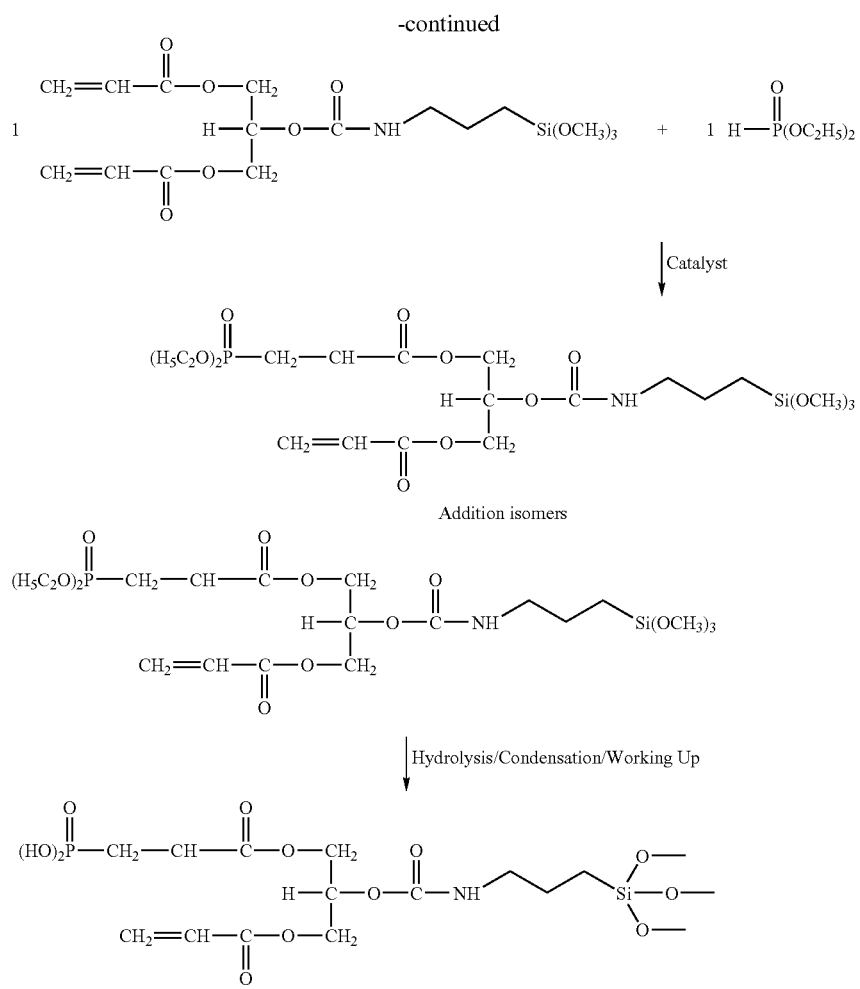

Under a dry atmosphere and stirring, 18.55 g (75.0 mmol) of 3-isocyanate propyl triethoxy silane are added dropwise to 17.12 g (75.0 mmol) glycerine-1,3-dimethacrylate and dibutyl tin dilaurate as addition catalyst. The course of the reaction (addition of the NCO group of the silane to the OH group of the methacrylate) is tracked by means of IR. Upon complete reaction, first 10.31 diethyl phosphite (75.0 mmol) are added at room temperature under a dry protective gas atmosphere and stirring, and subsequently a 25% sodium methanolate solution is added dropwise as the catalyst. The course of the reaction and thus the complete conversion of this exothermic PH addition can be proven by means of IR spectroscopy based on the following changes:

disappearance of the $v_{PH}$ bands at 2431 cm$^{-1}$
decrease of the $v_{CH}$ bands (olefin) at 3040 cm$^{-1}$
decrease of the $v_{C=C}$ bands at 1638 cm$^{-1}$ The resulting phosphonate-modified methacrylate silane (isomer mixture) can also be isolated in form of a viscous liquid through the usual processing or preferably directly reacted further.

EXAMPLE 3

Hydrolysis and condensation of the compound obtained in Example 2

For the hydrolysis and condensation of the above-mentioned reaction mixture about 75 ml acetic ester as well as aqueous HCl are added. The course of hydrolysis (e.g. Si(OC$_2$H$_5$)$_3$ and PO(OC$_2$H$_6$)$_2$ is tracked through the consumption of water by means of H$_2$O titration. Upon complete hydrolysis of the ethoxy groups, the resulting solution should be suitable e.g. for coating (with subsequent curing, i.e. polymerization of the methacrylate groups) any substrates.

The invention claimed is:

1. Compound of the Formula I

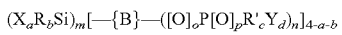

wherein the groups, radicals and indices have the following meanings:

B is an at least divalent, straight-chained or branched group with at least one organically polymerisable radical and at least four carbon atoms, X is a radical that can be cleaved from the silicon atom by hydrolysis, R and R' are independently alkyl, alkenyl, aryl, alkylaryl or arylalkyl wherein said alkyl, alkenyl, aryl, alkylaryl or arylalkyl is optionally substituted, Y is Cl, OH or OR', a is 0, 1, 2 or 3, b is 0, 1 or 2, a+b together are 1, 2 or 3, c is 0, 1 or 2, d is 0, 1 or 2, c+d together are 2, m is at least 1, with the proviso that m can only be 1 when a+b is 1 or 2, n is at least 1, o is 0 or 1, and p is 0 or 1.

2. Compound of the Formula I according to claim 1, wherein each X is independently hydrogen, halogen, hydroxy, alkoxy, acyloxy, alkylcarbonyl, alkoxycarbonyl or NR, and R" is alkyl with 1-4 carbon atoms or aryl with 6-12 carbon atoms.

3. Compounds of the Formula I according to claim 1, wherein B contains at least one norbornene, acrylate or methacrylate group.

4. Compounds of the Formula I according to claim 1, wherein the index o is zero.

5. Compounds of the Formula I according to claim 1, wherein the index o is equal to 1.

6. Compounds of the Formula I according to claim 5, wherein the index p is 1 and the index c is zero.

7. Method for producing compounds of the Formula I according to claim 1 wherein the index o is 0, comprising reacting a compound of the Formula II $$(X_aR_bSi)_m[-\{B^1\}]_{4-a-b} \qquad \text{II,}$$

wherein the radicals and indices X, R, a, b and m have the meanings as defined in Formula I according to claim 1 and B' is a derivative of the group B as defined in Formula I of claim 1 with one additional organic polymerisable group and has a valency that is lower by 1, with a compound of the Formula III $$H-P[O]_pR'_cY_d \qquad \text{III,}$$

wherein the radicals and indices R', Y, c and d have the meanings provided in Formula I of claim 1 and p is 1.

8. Method for producing a compound with Formula I according to claim 1 wherein the index p is 1 and the index c is 0, comprising reacting a compound of the Formula IV $$(X_aR_bSi)_m\{-B^2\}_{4-a-b} \qquad \text{IV,}$$

wherein the radicals and indices x, R, a, b and m have the meanings as defined in Formula I of claim 1 and $B^2$ is a derivative of the group B as defined in Formula I of claim 1 with one additional OH group and a valency that is lower by 1, in the presence of an alkaline catalyst with $POCl_3$, subsequently the developed HCl is removed, groups Y with the meaning Cl are converted into groups with the meaning OH or OR', and purifying the obtained compound with the Formula I.

9. Method for producing a compound of Formula I according to claim 1 wherein the index p is 1, the index c is 0, the radical Y is OH and the index d is 2, comprising reacting a compound of the Formula IV $$(X_aR_bSi_m[-\{B^2\}]_{4-a-b} \qquad \text{IV}$$

wherein the radicals and indices x, R, a, b and m have the meanings as defined in Formula I of claim 1, and $B^2$ is a derivative of the group B as defined in Formula I of claim 1 with one additional OH group and a valency that is lower by 1, with $P_2O_5$.

10. Method for producing a compound of Formula I according to claim 1 wherein the index o is 0, comprising reacting a compound of the Formula V $$(X_aR_bSi)_m[-\{B^3\}]_{4-a-b} \qquad \text{V,}$$

wherein the group $B^3$ is a derivative of the group B as defined in Formula I of claim 1 with one additional halogen atom and a valency that is lower by 1, with a phosphorous compounds of the formula VI, $$R'_cPY_d \qquad \text{VI}$$

wherein R' and Y have the meanings provided for Formula I in claim 1 and c is 0, 1 or 2, d is 1,2 or 3 and c+d is 3.

11. Silicic acid polycondensate that is obtained by the hydrolytic condensation of at least a compound of the Formula I $$(X_aR_bSi)_m[-\{B^7\}-([O]_oP[O]_pR'_cY_d)_n]_{4-a-b} \qquad \text{I,}$$

wherein the groups, radicals and indices have the following meanings:

$B^7$ is an at least divalent, straight-chained or branched radical with at least one organically polymerisable radical and at least 4 carbon atoms, X is a radical that can be cleaved from the silicon atom by hydrolysis, R and R' are independently alkyl, alkenyl, aryl, alkylaryl or arylalkyl wherein said alkyl, alkenyl, aryl, alkylaryl or arylalkyl is optionally substituted, Y is Cl, OH or OR', a is 0, 1, 2 or 3, b is 0, 1 or 2, a+b together are 1, 2 or 3, c is 0, 1 or 2, d is 0, 1 or 2, c+d together are 2, m is at least 1, with the proviso that m can only be 1 when a+b is 1 or 2, n is at least 1, o is 0 or 1, and p is 0 or 1, and wherein the hydrolytic condensation optionally comprises further hydrolysable and condensable silanes and/or further hydrolytically condensable compounds of elements selected from the group consisting of B, Al, F, Sn, Pb, the transition metals, the lanthanides and the actinides.

12. Silicic acid polycondensate according to claim 11, wherein the group $B^7$ contains one or more organically polymerisable radicals, each X is independently hydrogen, halogen, hydroxy, alkoxy, acyloxy, alkylcarbonyl, alkoxycarbonyl or NR" and the substituent R" is alkyl with 1-4 carbon atoms or aryl with 6-12 carbon atoms.

13. Silicic acid polycondensate according to claim 12, wherein the group $B^7$ contains at least one norbornene, acrylate or methacrylate group.

\* \* \* \* \*